United States Patent [19]

Monsigny et al.

[11] Patent Number: 4,801,578

[45] Date of Patent: Jan. 31, 1989

[54] MURAMYLPEPTIDE-GLYCOPROTEIN IMMUNOSTIMULANT DERIVATIVES, THEIR PREPARATION AND THEIR USE IN MEDICATION

[75] Inventors: Michel Monsigny, Saint-Cyr-en-Val; Annie-Claude Roche, Saint-Pryve, both of France

[73] Assignee: Establishment Public dit Centre National de la Recherche Scientifique (CNRS), Paris, France

[21] Appl. No.: 617,176

[22] Filed: Jun. 4, 1984

[30] Foreign Application Priority Data

Jun. 3, 1983 [FR] France ............................ 83 09325

[51] Int. Cl.[4] .................. C07K 15/14; C07K 9/00; A61K 37/02; A61K 45/05
[52] U.S. Cl. ................................ 514/8; 424/85.8; 424/88; 424/89; 530/322; 530/395; 530/397
[58] Field of Search ............... 260/112 R, 112.5 R; 424/85, 88, 89; 530/322, 395, 397; 514/8

[56] References Cited

U.S. PATENT DOCUMENTS

| | | | |
|---|---|---|---|
| 4,235,771 | 11/1980 | Adam et al. ................. | 260/112.5 R |
| 4,314,998 | 2/1982 | Yamamura et al. ..... | 260/112.5 R X |
| 4,317,771 | 3/1982 | Shiba et al. ................. | 260/112.5 R |
| 4,395,399 | 7/1983 | Ovchinnikov et al. ................. | 514/8 |
| 4,401,659 | 8/1983 | Le Francier et al. ................. | 514/8 |
| 4,446,128 | 5/1984 | Baschang et al. .......... | 260/112 R X |
| 4,639,512 | 1/1987 | Audibert et al. ................. | 424/88 X |

FOREIGN PATENT DOCUMENTS 2912865 10/1979 Fed. Rep. of Germany ........ 424/88

OTHER PUBLICATIONS

Nature, 285, p. 66 (1980), Goldstein et al.

*Primary Examiner*—Howard E. Schain
*Attorney, Agent, or Firm*—Cushman, Darby & Cushman

[57] ABSTRACT

Macromolecular conjugates of muramylpeptides useful as a stimulant of the cellular immune systems have the formula $(R-X)_m-(LAM)$ wherein R is an N-acetylmuramylpeptidyl group or a derivative thereof; (LAM) is a neoglycoprotein having affinity for macrophages or monocytes, consisting of a protein covalently substituted by more than five glycidic chains, each having at least five osidic units, X is a covalent bond between a functional group of the peptidic part of R and a functional group of (LAM) or X is the residue of a conventional bifunctional coupling agent capable of bonding to R and (LAM) by formation of covalent bonds; and m is a number greater than or equal to 1.

9 Claims, 2 Drawing Sheets

MURAMYLPEPTIDE-GLYCOPROTEIN IMMUNOSTIMULANT DERIVATIVES, THEIR PREPARATION AND THEIR USE IN MEDICATION

This invention relates to new immunostimulant derivatives, their preparation and their use in medication.

It is known that numerous extracts of mycobacteria, such as the soluble fraction of their cell walls (WSA) and their synthetic counterparts such as muramyldipeptide (MDP) have an adjuvant effect comparable to those of the mycobacteria in Freund's complete adjuvant. MDP is of particular interest, since it can be synthesized (C. Merser et al., 1975, Biochm. Biophys. Res. Commun. 66, 1316-1322) and because of this, it is available in unlimited quantities; in addition, it has a low molecular weight (492) and it is non-toxic. The biological properties of MDP and its numerous derivatives include adjuvant activity, general stimulation of the immune system and resistance to infections (see articles by Adam, A. et al., 1981, Mol. Cell. Biochem. 41, 27–47; Leclerc, C. and Chedid, L., 1982, in Lymphokines E. Pick ed., Academic Press, Vol. 7., pp. 1–21.

It is known that muramylpeptide in vitro acts on cells of the reticuloendothelial system (macrophages) by increasing their phagocytic activity (Tanka et al., 1977, Biochem. Biophys. Res. Commun, 77, 621–627).

MDP and the various other mycobacteria extracts also increase cytotoxic and cytolytic activity in the periotoneal macrophages in mice in vitro (Juy, C. and Chedid, L., 1975, Proc. Nat. Acad. Sci. 72, 4105-4109). Although MDP in relatively low concentrations (10 μg/ml) produces a cytostatic effect of macrophages on tumor cells in vitro, it cannot be used directly in vivo because it is very rapidly excreted through the urine (50% after 30 minutes and over 90% after two hours) in mice (Parant et al., 1979 Int. J. Immunopharmacol. 1, 35-41). In order to increase the lifespan of MDP in the organism, various oligomers and polymers which are not specific to target cells have been developed, and some of these display a certain amount of activity. More specifically, Chedid, L. et al., (1979, Proc. Nat. Acad. Sci. 76, 6557-6561) have demonstrated that MDP linked to a multipolymer (multi-poly-D-L-alanine-poly-L-lysine) induces an increased resistance to infection but also produces a significant pyrogenic effect.

The object of this invention is new macromolecular conjugates of muramylpeptides and their analogs. These derivatives are immunostimulant; some of these are not only more active than the free immunostimulants (MDP, derivatives and counterparts) in the induction of tumoricide in macrophages in vitro, but also eradicate the spontaneous metastasis of pulmonary carcinoma in mice, in vivo, while free immunostimulant are ineffective.

More specifically, the object of this invention is new derivatives of general Formula I:

(I)

wherein

R is the residue of an immunostimulant of the N-acetylmuramylpeptide type or a derivative or counterpart thereof, (LAM) is an affinity ligand of the macrophages or monocytes, or a precursor of such a ligand, and X represents either a covalent bond between R and (LAM) or the residue of a bonding agent to bond R to the ligand (LAM), and m is a number which is greater than or equal to 1.

The maximum value of number m is variable and is determined in each case using simple experiments, as shall be disclosed below.

Among the formula compounds, the following shall more specifically be cited:

(A) Those compounds for which R represents the residue of a compound comprising the N-acetylmuramyl-L-Ala, particularly the sequence:
N-acetylmuramyl-L-Ala-D-iso-Gln- or
N-acetylmuramyl-L-Ala-D-Glu-.

R may be, for example, the residue of one of the MDP derivatives cited in the article by Adam, A., et al., 1981, Mol. Cell. Biochem. 41, 24–47, and, more specifically, R may represent the residue of:

MDP (N-acetylmuramyl-L-Ala-D-isoGln)
MTP (N-acetylmuramyl-L-Ala-D-isoGln-meso-$A_2$pm)
MQP (N-acetylmuramyl-L-Ala-D-isoGln-meso-$A_2$pm-D-Ala)
MPP (N-acetylmuramyl-L-Ala-D-isoGln-meso-$A_2$pm-D-Ala-D-Ala)

or a muramylpeptide residue substituted by an amino acid, a peptide, a bifunctional group, by glutaraldehyde, p-thiocarbamyl benzoic acid, etc.

In the above, Ala- is the symbol for the alanyl group; meso-$A_2$pm represents the mesodiaminopimelyl group and isoGln represents the isoglutaminyl group.

(B) Those for which (LAM) represents:

(1) glycoconjugates selectively recognized by the membrane lectins of the macrophages or the monocytes, and more specifically:

(a) natural or modified glycoproteins carrying glucosidic structures containing, for example, residues of α-D-mannose, 6-phosphoryl α-D-mannose, or β-N-acetylgulcosamine; natural glycoproteins are described, for example, in the work by Jean Montreuil, "Glycoproteins," in Comprehensive Biochemistry, Vol. 19, B2, Albert Neuberger Ed. (Elsevier), 1982.

(b) oligosaccharides or glycopeptides containing at least one of the residues of α-D-glucopyranoside, α-D-mannopyroanoside, α-L-fucopyranoside, (α or β)-L-galactopyranoside, β-D-galactopyranoside, 2-acetamido-2-deoxy-(α or β)-D-glucopyranoside, 2-acetamido-2-deoxy-α-D-galactopyranoside, 2-acetamido-2-deoxy-β-D-galactopyranoside, 6-phosphoryl-α-D-mannopyranoside, or α-L-rhamnopyranoside. The oligosaccharides employed according to this invention are, specifically, the oligosaccharides released from natural glycoproteins by endoglycosidases, or synthetic counterparts of these oligosaccharides.

It is known that in order to be recognized by the membrane receptors, oligosaccharides must contain at least five osidic units. For this reason, according to this invention, oligosaccharides and oligopeptides containing at least five osidic units, for instance oligosaccharides or oligopeptides comprising from 5 to 18 osidic units shall be employed. The glycopeptides employed according to this invention are, more specifically, glycopeptides obtained from natural glycoproteins. These glycopeptides are described by J. Montreuil (in the article cited above). They may be prepared by enzymatic processing of the natural glycoproteins according to the methods described, for example, by Monsigny et al., Bull. Soc. Chim. Biol. Vol. 50, pp. 857–886; or else, synthetic or semi-synthetic glycopeptides similar to the glycopeptides obtained according to said enzymatic processing of natural glycoproteins are employed. According to custom, "glycopeptide" in this context is the name used for a derivative formed of a glucosidic chain bonded to at least one amino acid, which, more specifically, is asparagine, serine or threonine for reasons which shall be made apparent below.

The saccharidic unis of the oligosaccharides and/or the glycopeptides employed according to the invention may be subjected to partial esterification, for instance in the form of phosphates.

(c) neoglycoproteins, that is, proteins substituted by glycidic copula.

Neoglycoproteins are obtained as described in the work of Lee, Y. C. and Lee, R. T., 1982, in the Glycoconjugates, M. I. Horowitz, Ed., Academic Press, Vol. 4, Pages 57–83.

The base proteins are preferably syngenic proteins, such as, for example, serum albumin, lysozyme, ferritin, an immunoglobulin etc.

It is known that in natural glycoproteins, the glucosidic chains are combined to an amino acid of the protein—either to asparagine by an amide bond, or to an alcohol amino acid (serine, threonine, hydroxyproline) by an osidic bond. These bonds are schematically represented by the following partial formulae:

asparagine bond:

alcohol amino acid bond (case of serine):

Of course, in the neoglycoproteins, the glucosidic chains may be connected to the peptidic chains through the same amino acids. In these neoglycoproteins, each glucosidic chain introduced preferably comprises five osidic units.

The minimum number of glycidic copula bonded to the protein is experimentally determined in each case by the floor at which an affinity of the neoglycoprotein for the macrophages or monocytes is displayed, wherein this affinity must be sufficient to provide for efficient endocytosis (for instance, when neoglycoprotein is used in a concentration of less than one micromole per liter).

This minimum value is normally greater than 5.

Specialists in the field will understand that, in general, with respect to the maximum number of fixed glycosidic copula, that there is no maximum level other than that which corresponds to saturation of the reactive bonding sites on the protein.

The glucosidic copula are selected in particular from among the osides of α-D-glucose, α-D-mannose, α-L-fucose, N-acetylglucosamine, α-L-glucose, β-L-galactose, β-D-galactose, α-D-galactosamine, β-D-galactosamine, α-L-rhamnose or 6-phosphoryl-α-D-mannose, and comprise a group which provides for establishment of a covalent bond with the protein (for instance, an isothiocyanate group, a diazophenyl group, a thioethanoyl group, etc.)

To prepare the neoglycoproteins, a method similar to that described by McBroom, et al, Met. Enzymol., 28, 212–219 (1972) may be employed, for example. It consists of preparing a nitrophenylated derivative from a saccharide and of reducing the nitrophenyl group to a primary phenylamine. The primary amine group may then be transformed into an isothiocyanate group and the resulting product bonded onto the selected protein, wherein this bond is achieved by reaction of the phenyl isothiocyanate with the amino groups of the protein, with formation of a phenylthiocarbamyl group. The derivative of the primary phenylamine group may also be transformed into the corresponding diazonium salt. The resulting product may then be bonded onto the selected protein, wherein this bond is achieved by formation of an azoic derivative with certain of the protein's amino acids, which contain activated aromatic groups (specifically, tyrosine, tryptophan), or by reaction comprising an amine group such as in lysine, a guanidine group such as in arginine or an imidazol group such as in histidine.

Among the neoglycoproteins, those containing osides from among those listed below are specifically cited:
a thiocarbamylphenyl-α-D-glucopyranoside residue
a thiocarbamylphenyl-β-D-galactopyranoside residue
a thiocarbamylphenyl-α-D-mannopyranoside residue
a thiocarbamylphenyl-2-acetamido-2-deoxy-β-D-glycopyranoside residue
a thiocarbamylphenyl-α-L-fucopyranoside residue
a thiocarbamylphenyl-α-D-galactopyranoside residue
a thiocarbamylphenyl-α-L-rhamnopyranoside residue
a thiocarbamylphenyl-6-phosphoryl-α-D-mannopyranoside residue
a thiocarbamylphenyl-2-acetamido-2-deoxy-α-D-glucopyranoside residue
a thiocarbamylphenyl-2-acetamido-2-deoxy-α-D-galactopyranoside residue
a thiocarbamylphenyl-2-acetamido-2-deoxy-β-D-galactopyranoside residue
a thiocarbamylphenyl-β-D-galacto-pyranosyl-4-β-D-glucopyranoside residue
an azophenyl-β-D-galactopyranosyl-4-β-D-glucopyranoside residue
an azophenyl-α-D-glucopyranoside residue
an azophenyl-α-D-mannopyranoside residue
an azophenyl-α-L-fucopyranoside residue
an azophenyl-βD-galactopyranoside residue
a azophenyl-2-acetamido-2-deoxy-β-D-glycopyranoside residue
the residues of oligosaccharides or of glycopeptides encompassing at least one residue of the following:
α-D-glucopyranoside, α-L-glucopyranoside, α-D-mannopyranoside, α-L-fucopyranoside, β-L-galactopyranoside, β-D-galactopyranoside or 2-acetamido-2-deoxy-β-D-galactopyranoside, 2-acetamido-2-deoxy-β-D-galactopyranoside, 2-acetamido-2-deoxy-β-D-galactopyranoside, 6-phosphoryl-α-D-mannopyranoside, α-L-rhamnopyranoside.

(d) natural or modified polysaccharides containing residues of α-D-glucose, α-D-mannose, α-L-fucose or N-acetylglucosamine.

Among these polysaccharides can be mentioned, for example, yeast polysaccharides (particularly mannan), bacteria polysaccharides (particularly *Escherichia coli*, Salmonella, Klebsiella bacteria) or other polysaccharides (fucoidin, lentinan, etc.).

(2) The proteins modified by substitutions which lower the isoelectric point, either by blocking of the free amine groups, or by incorporating carboxylic groups, or by one method or another (see, for example, Science, Vol. 218, 1982, pp. 574–576).

From among these modified proteins, the following may be mentioned: the N-acylated proteins (such as succinylated, maleylated, citraconylated, aconitylated, acetylated, etc. proteins), the S-carboxymethylated proteins, etc.

For modifications of these proteins, see, for example, Methods in Enzymology, Vol. XI and Vol XXV (Academic Press).

The base proteins used are preferably syngenic proteins;

(3) antiproteases such as $\alpha_2$-macroglobulin, $\alpha_1$-antitrypsine and, more generally, the conventional syngenic seric anti-proteases which are described, for example, in Methods in Enzymology, Vol. 80 (Academic Press).

These antiproteases must be considered to be precursors of affinity ligands of the macrophages because they spontaneously form complexes with numerous proteases (and particularly with proteases secreted by tumor cells). It is known that these protease-antiprotease compounds have an affinity for macrophages or monocytes; see, for example, Jerry Kaplan et al., The Journal of Biological Chemistry, Vol. 254, No. 15, 7329–7335 (1979).

(4) anti-tumor cell antibodies (and particularly monoclonal antibodies) which will form compounds in the organism with soluble or membranary antigens of these cells.

It is well known that these complex compounds are recognized selectively by the macrophages.

These antibodies therefore constitute the precursors of affinity ligands of macrophages:

(C) Those for which X represents a covalent bond bvetween a functional group of the peptidic part of R and a functional group of (LAM); or those for which X is the residue of a usual bonding agent (bifunctional molecule) enabling R to be bonded to (LAM) by establishment of covalent bonds. Formula I compounds.

This process is characterized by the fact that the derivative (R) corresponding to the residue R is made to react with the ligand (LAM), potentially in the presence of a bonding agent, using conventional methods.

As a variation, either (R) or (LAM) may be made to react with one of the reactive functions of the bonding agent (the other function may potentially be temporarily blocked), then the resulting product, of the RX or $(X)_m$—LAM, is made to react with (LAM) or (R) respectively.

With respect to the number m of (R) molecules in the reaction process with the (LAM) molecule, this number, as previously indicated, is at least equal to 1. The maximum value of this number m is determined for each case: (a) by observation of the loss from the selective recognition phenomenon of the substituted LAM vis-a-vis the macrophage receptors (due to saturation of the recognition sites of the LAM molecule by the RX-substitutes); or (b) similarly, in the case where LAM is an antibody, by the loss of capacity of the substituted LAM to bond to the corresponding agent; or (c) similarly, in the case where LAM is an antiprotease, by the loss of capacity of the substituted LAM to bond the proteases. This maximum value for m can therefore easily be determined by simple routine in vitro experiments in each case.

In general, the amine groups (when these are present) of the MDP derivative may be made to react with carboxylic groups (in activated form) of the ligand (LAM). Of course, it is possible to cause to appear on the ligand (LAM) carboxylic groups or to increase their numbers. For example, if the (LAM) ligand is a protein, a glycoprotein or a neoglycoprotein, it is possible to cause carboxylic groups to appear by the effect of a carboxylic diacid derivative, for instance by succinylation. The free carboxylic groups of the resulting derivative are then appropriately activated to react with the $NH_2$ groups of the MDP derivative which is thus bonded with formation of an amide bond.

Conversely, it is possible to make the amino groups of the ligand (LAM) react with the carboxylic groups of the MDP derivative (for instance the iso-Gln carboxylic group). In this case, it is possible to cause additional amino groups to appear on the ligand; for example, if the ligand is a protein, a glycoprotein or a neoglycoprotein, it may be succinylated then the succinylated derivative can made to react with a diamine, according to a method similar to the above described method. In this way, hydrazides of the amino acids of the ligand may be formed by the action of the hydrazine.

When the ligand (LAM) is an N-acylated protein, the protein can also be bonded to the MDP derivative before acylation of the protein. Several non-limiting examples are provided below to illustrate the bonding of the ligand (LAM) onto the MDP derivative. For example, to bond an oligosaccharide or a polysaccharide to MDP (or one of its derivatives), primary amino groups may be introduced into the saccharide by making it react with an aminoethylsulfate; or saccharide is made to react with a bromoacetate, then the resulting acetic ester is made to react with a diamine (fon example, ethylenediamine) so as to obtain a corresponding amino-ethyl-monoamide. An amine group may also be introduced onto the polysaccharide by esterizing alcohol groups of the polysaccharide with carbonyldiimidazole, then making the resulting product react with a diamine to produe, as previously, a corresponding aminated derivative of the polysaccharide. For example, with ethylenediamine, a derivative of the Sacch. —O—CO—NH—$(CH_2)$—$NH_2$ is obtained (where Sacc. is the remainder of the polysaccharide). The resulting aminated derivative may then be made to react to produce an amide bond with a carboxyl group of the MDP derivative (for example, the carboxyl group of iso-Gln), wherein said carboxyl group is of course activated in accordance with the normal methods (for example, in the form of a hydroxysuccinimide ester). Alternatively, the technique using bromoacetate will cause to appear on the saccharide a carboxylic group which will react with the amine gorups of the derivative and will thus allow the saccharide to be bonded onto the MDP derivative by establishing an amide bond.

Of course, the methods described above for the oligosaccharides are applicable to the glycopeptides. A carboxylic group may also be introduced on a saccharide (or oligosaccharide or polysaccharide) in the form of a 1-deoxy 1-carboxyalkylthio pyranoside derivative.

For example, beginning with the corresponding 1-chloro pyranoside (the hydroxyl groups of which are conveniently protected in the form of benzoates), the corresponding 1-isothiouronium chloride is produced by the action of thioride. The action of methyl bromoacetate in the presence of sodium dithionite produced the corresponding methyl 1-thioethianoate derivative, which may be debenzoyled. This methylic ester may then be saponified into the corresponding carboxylic derivative and the carboxylic group is activated (for example, for formation of hyroxysuccinimide ester). The active thioethanoic derivative obtain may be made to react, for example, with amine groups (if these are present) of the MDP derivative.

A similar process of thioethanoylation of a saccharidic derivative is described, for example, in French patent application No. 83 14179 filed on Sept. 5, 1983, entitled "New Furanose Derivatives, their Preparation and their Application."

Thus, —NH$_2$ groups may be made to appear on oligosaccharides containing N-acetyl osamine units (for example, N-acetylglucosamine) by hydrazinolysis.

To bond the MDP derivative onto an antibody, a bifunctional bonding agent may be used, for example, or the body may be made to react with an activated ester of the MDP derivative (bonding by establishing an amnide bond with the NH$_2$ gorups of the antibody), etc.

As indicated above, Formula I compounds display interesting pharmacological properties. Together with limited toxicity, these properties make them suitable for use as medication.

Therefore, a still further object of the invention is the use of Formula I derivatives in medication.

The medications according to the invention are stimulants of the cellular immune system and induce a protective and therapeutic effect, particularly with respect to bacterial infections and the development of tumor cells, and especially spontaneous metastasis cells.

The invention extends to pharmaceutical compositions containing at least one Formula I medication. These compositions are prepared according to conventional methods.

These pharmaceutical compositions may be administered by intravenous injection, intra-tumor injection or by inhalation.

For this purpose, they may be prepared in the form of solutions or suspensions suitable for injection, or in the form of solutions or suspensions for aerosol sprays.

The posology varies depending on the method of administration, body weight, and the ailment under treatment. For intravenous injection, for example, the dosage is on the order of 50 micrograms to 500 micrograms (weight of MDP or counterpart) per kg.

The examples which follow are non-limiting embodiments of the invention.

EXAMPLE 1

Neoglycoprotein of the type: ($\alpha$-Man-PTC)$_{25}$-serum albumin-(MDP)$_{20}$.

(a) Bovine serum albumin (MM 67000; 50 mg) is dissolved in 5 ml of sodium carbonate buffer 0.10M, pH 9.3 at 4° C. To this solution are added 40 mg of O-phenylisothiocyanate$\alpha$-D-mannopyranoside (prepared in accordance with McBroom, et al., 1972, Met. Enzymol. 28, 212–219). After 10 hours of agitation at 4° C., the neoglycoprotein is purified by molecular filtration on a GF05 Ultrogel column (3×40 cm), and the fractions containing the neoglycoprotein are dialyzed using distilled water, then lyophilized.

(b) Muramyldipeptide (N-acetylmuramyl-L-alanyl-D-isoglutamine (30 mg., 60 micromoles) is dissolved in 0.6 ml. of freshly distilled N-dimethylformamide on fluorodinitro benzene. The solution is kept at 4° C. and 1.2 equivalents of dicyclohexyl carbodiimide (15 mg., 72 micromoles) and 1.2 equivalents of N-hydroxysuccinimide (8.3 mg; 72 micromoles) are added. The solution is agitated for 24 hours. The progress of the reaction is followed by thin layer chromatography in silica gel (solvent mixture: ratios of chloroform:methanol:acetic acid:water, 2:2:1:1, vol/vol). Rf of the MDP: 0.57, Rf of MDP—O—Su: 0.67. The cyclohexyluric precipitate is removed by centrifugation (10 min., 2,000 g.) or by filtration on heated glass.

Note: MDP—O—Su signifies: hydroxysuccinimide ester of MDP.

(c) The activated muramyldipeptide solution (MDP—O—Su) (60 $\mu$l containing 3 mg of MDP) is added to a solution of neoglycoprotein (Man)$_{25}$—SAB (5 mg in 150 $\mu$l of sodium acetate 1M, pH 8.5). The reaction mixture is agitated for 24 hours at 25° C. The immunogen, (Man)$_{25}$—SAB—(MDP)$_{10}$, is purified by molecular filtration on a GF05 Ultrogel column in buffered physiological serum. The fractions containing the immunostimulant, (Man)$_{25}$—SAB—(MDP)$_{10}$, are regrouped, the solution is then sterilized by filtration on Millipore (0.2 m) and kept at −20° C. As an alternative, the solution may be dialyzed then lyophilized.

Note: PTF signifies: phenylthiocarbamyl. The notation ($\alpha$-Man)$_{25}$ is also used, omitting the "PTC" bonding agent residue designation, which in this case is implied. SAB signifies: bovine serum albumin.

EXAMPLE 2

Neoglycoprotein of the type: ($\alpha$-Man)$_{25}$-serum albumin-(MDF)$_{20}$. This immunostimulant is prepared using a method identical to that described in Example 1, except that the quantity of MDP—O—Su added in step 1c is 6 mg in MDP in 60 microliters of dimethylformamide.

Note: Of course, in this case, ($\alpha$-Man) in fact represents ($\alpha$-Man-PTC).

EXAMPLE 3

Neoglycoprotein of the type: ($\alpha$-GLc)$_{28}$-serum albumin-(MDP)$_{20}$.

This immunostimulant is prepared using a method identical to that described in Example 1, except that O-phenyl isothiocyanate of $\alpha$-D-glucopyranoside is used instead of the $\alpha$-D-mannopyranoside derivative.

Note: ($\alpha$-Glc) represents, more accurately, ($\alpha$-Glc-PTC).

EXAMPLE 4

Neoglycoprotein of the type: ($\alpha$-Fuc)$_{32}$-serum albumin-(MDP)$_{10}$.

The same procedure as that described in Example 3 is followed, substituting O-phenyl isothiocyanate of $\alpha$-L-fucopyranoside. Here again, ($\alpha$-Fuc) is an abbreviated notation for ($\alpha$-Fuc-PTC).

EXAMPLE 5

Neoglycoprotein of the type: ($\beta$-GlcNAc)$_{25}$-serum albumin-(MDP)$_{10}$.

The same procedure as that described in Example 3 is followed, substituting O-phenyliso thiocyanate of 2-acetamido-2-deoxy-$\beta$-D-glycopyranoside.

Note: ($\beta$-GlcNAc) more accurately represents ($\beta$-GlcNAc-PTC).

EXAMPLE 6

Neoglycoprotein of the type: ($\beta$-Gal)$_{30}$-serum albumin-(MDP)$_{10}$.

The same procedure as that described in Example 3 is followed, substituting O-phenyl isothiocyanate of β-galactopyranoside. For the notation, see notes for preceding examples.

EXAMPLE 7

Neoglycoprotein of the type: (β-Lac)$_{28}$-serum albumin-(MDP)$_{10}$.

The same procedure as that described in example 3 is followed, substituting O-phenylisothiocyanate of β-lactopyranoside. For the notation, see notes for preceding examples.

EXAMPLE 8

Neoglycoprotein of the type: (di-N-acetylchitobioside)$_{20}$-serum albumin-(MDP)$_{10}$. The same procedure as that described in example 3 is followed, substituting O-phenyl isothiocyanate of 2-acetamido-2-deoxy-4(1-acetamido-2-deoxy-β-D-glycopyranosyl)-β-D-glycopyranoside. Of course, (di-N-acetylchitobioside) is an abbreviated notation for (di-N-acetylchitobioside-PTC).

EXAMPLE 9

Neoglycoprotein of the type: (α-Man)$_{20}$-serum albumin (MDP($_{10}$.

(a) The neoglycoprotein is prepared by action of O-diazophenyl-D-mannopyranoside chlorhydrate under the previously described conditions (FEBS Letters, 1977, 76, 257-261).

Steps (b) and (c) are identical to those described in 1b and 1c.

Note: Of course, (α-Man) is an abbreviated notation for (azophenyl-α-Man).

EXAMPLE 10

Neoglycoprotein of the type: (α-Man)$_{25}$-serum albumin (MPP)$_{10}$.

(a) The neoglycoprotein is prepared according to the method described in 1a. (α-Man) therefore signifies (α-Man-PTC) in this case. Next, the neoglycoprotein (20 mg) is dissolved in 5 ml of saturated sodium acetate. To this solution is added 10 mg of succinic anhydride. After 12 hours of agitation, the succinylated neoglycoprotein is dialyzed against distilled water and then lyophilized.

(b) the syccinylated neoglycoprotein is dissolved in 10 ml of anhydrous N-dimethylformamide. To this solution is added dicyclohexylcarbodiimide (5 mg, 24 micromoles), then hydroxysuccinimide (2.8 mg; 24 micromoles) at 4° C. After 24 hours of agitation at ambient temperature, 5 mg of N-acetylmuramil pentapeptide in 5 ml of 0.1M sodium carbonate buffer solution is added. The reaction mixture is agitated for 18 hours at 4° C. The immunogen (α-Man)$_{25}$-serum albumin-(MPP)$_{10}$ is purified by molecular filtration chromatography in an AcA 202 Ultrogel column, stabilized in a PBS pH 8.5 buffer. The immunogen is then sterilized by filtration and lyophilized.

EXAMPLE 11

Monoclonal-(MDP)$_{40}$, LLC cell-specific antibody.

A monoclonal mouse antibody, specific to the Lewis pulmonary carcinoma cells (the IgM 6 B6 antibody) is dissolved (4 mg/ml) in a molar sodium acetate buffer of pH 8.5. To this solution the MDP—O—Su described in Example 1b is added, and the reaction is conducted as in Example 1c. The monoclonal-(MDP)$_{40}$ is purified by molecular filtration on an AcA 202 Ultrogel column. The fractions containing the monoclonal-(MDP)$_{40}$ antibody are sterilized by filtration over Millipore (0.22μ), then kept at 4° C.

The same experiment was performed on the 5B5 monoclonal antibody.

EXAMPLE 12

Monoclonal-(MDP)$_{20}$, L1210 cell-specific antibody.

A monoclonal (IgM F2-10-23) mouse antibody, specific to L1210 leukemia cells, is processed according to the procedure described in Example 11.

EXAMPLE 13

Mannan-(MDP)$_{20}$.

*Saccharomyces cerevisae* mannan (50 mg) is dissolved in 10 ml of dimethylsulfoxide. To this solution are added 10 mg of carbonyldiimidazol. After 1 h at 4° C., 0.1 ml of diamine ethylene is added. After 20 hours of agitation at 4° C., the substituted mannan is purified by molecular filtration. The substituted mannan is then processed with MDP—O—Su following the procedure described in Example 1c.

Of course, in this example, (MDP) is an abbreviated notation in which is omitted the designation of the bonding agent X which represents, in this instance, —CO—NH—C$_2$H$_4$—NH—.

EXAMPLE 14

Neoglycoprotein of the type: (α-Man)$_{25}$—SAB—(MDP)$_{18}$.

Following a procedure similar to that described in Example 1, a conjugated neoglycoprotein of the type (α-Man)$_{25}$—SAB—(MDP)$_{18}$ was prepared. The notation (α-Man)$_{25}$ in this case is an abbreviation for (α-Man-PTC)$_{25}$.

EXAMPLE 15

Neoglycoprotein of the type: (6-P-α-Man)$_{20}$—SAB—(MDP)$_{15}$.

Following a procedure similar to that described in Example 1, this neoglycoprotein, (6-P-α-Man), which means (6-phosphoryl-α-Man), is an abbreviated notation for (6-P-α-Man-PTC) was prepared.

STUDY OF PHARMACOLOGICAL PROPERTIES (A) Activation of tumor death of macrophages in vitro.

(1) Target cells

L1210: Leukemic cells of mice (DBA/2) maintained in culture, in suspension in a MEM medium containing 10% of horse serum. These are used in exponential growth phase (5.7×10$^5$ cell/ml).

Lewis LLC pulmonary carcinoma cells: These are produced by a tumor which develops spontaneously in C57 BL6 mice and generate numerous pulmonary metastases. These cells are cultivated in single layers (seeded at 2×10$^4$ c/ml) in a MEM culture medium containing 20% bovine foetal serum at 37° C., in a 5% CO$_2$ atmosphere. At confluence (after three days) they are recovered by brief processing with a solution of 0.02% EDTA in PBS buffer containing 0.1% glucose, then collected in the full medium. Viability >95%.

(2) Macrophages

Peritoneal macrophages of BDF$_1$ mice, induced by 1 ml. of thioglycolate medium (Pasteur Institute). Four days after injection, the mice are decapitated and the peritoneal cells are recovered by washing with the RPMI 1640 culture medium containing 5% SVF (SVF: veal foetal serum). After two washings, the cells are placed in suspension in the RPMI 1640 medium, 10% SVF, which contains the antibiotics and 0.1% of glutamine. $1-1.5 \times 10^7$ cells per mouse are recovered, and 80–90% of these are macrophages identified with the use of neutral red dye.

(3) Measurement of the cytostatic effect

In a microtitration plate (Microtest II beaker) $4 \times 10^5$ macrophages are incubated for 4 hours at 37° C. (5% $CO_2$); after three washings to eliminate the loose cells, the macrophages are incubated either with the stimulant (100 microliters) (MDP, MDP bonded to a neoglycoprotein or to a polysaccharide or to a polyclonal or monoclonal antibody), or with the corresponding control solutions (carrier protein, PBS), in RPMI 10% SVF, antibiotic, glutamine and 20% Hepes buffer, for 24 hours at 37° C. (5% $CO_2$). After three washings, the target cells are added to different concentrations to obtain varied macrophage/target cell rations (7 to 80). After 20 hours of incubation, tritiated thymidine is added (0.1Ci, 3.7 KBq$^3$H-thymidine, (CEA) 0.74–1.1 TBq/mmole.

The thymidine may also be added at the same time as the target cells. The cells are recovered on a fiberglass filter and washed using a device of the Mash II type. The radioactivity of the cells is measured by a beta meter after dissolution in a scintillating liquid (Tenu et al., 1980, Eur. J. Immunol. 10, 647–653.

$$\text{Inhibition percentage} = \frac{R - S}{R} \times 100$$

where
R = target cells + non stimulated microphages
S = target cells + stimulated macrophages.

The study of macrophage activation by the anti-tumor cell antibodies bonded to MDP (or to its derivatives) is performed by simultaneously comnbining the macrophages, the target cells and the stimulants. The cytostatic effect is measured after 24–48 hours of culture.

(4) Measurement of the cytotoxic effect

This effect is measured by broadening the radioactivity of target cells that have been specially marked before combining them with the macrophages (Raz et al., 1979, Cancer Immunol. Immunother. 7, 157). The target cells in the exponential growth phase are marked by incubation for 24 hours in a medium containing 0.2Ci (7.4 KBq)/ml of ($^{125}$I)IUdR, that is, 5-($^{125}$I)Iodo-2'-deoxyuridine Amersham 5Ci/mg, 185 GBq/mg. The cells are washed and added to the stimulated and non stimulated macrophages. The marked target cells are also incubated by themselves, for use as controls.

After 24 to 48 hours, the cultures are washed, then the adhering cells are lysated (0.1 ml 0.5NaCl) and washed. The resulting lysation and washing products are collected and radioactivity is measured by a scintillation gamma counter. The percentage of cytotoxicity mediated by the activated macrophages is then calculated:

$$\% \text{ cytotoxicity} = \frac{100 \times Cpm(Mn) - Cpm(Ms)}{Cpm(Mn)}$$

Cpm (Mn) means: number of strokes per minute for the target cells cultivated with normal macrophages.

Cpm (Ms) means: number of strokes per minute for the target cells cultivated with stimulated macrophages.

Results: after 36 hours, the free MDP has no effect. Conversely, the product examined (Man)$_{25}$—SAB—(MDP)$_{18}$ kills 50% of the LLC cells ($^{125}$I-UdR) at 1 g/ml.

Note: The LLC cells are also known as "3LL" cells.

(5a) Application to the measurement of the cytostatic effect of macrophages stimulated by Man-SAB-MDP.

Figure 1:
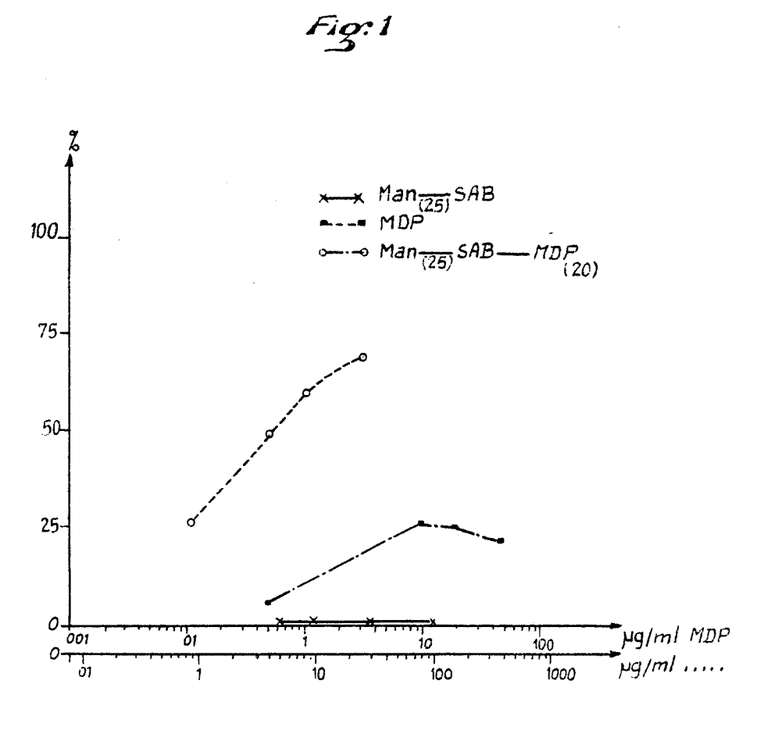
FIG. 1 represents the cytostatic effect of the peritoneal macrophages of mice treated with differing doses of free MDP or MDP conjugated to a neoglycoprotein (Man-SAB) on L1210 target cells.
Figure 2:
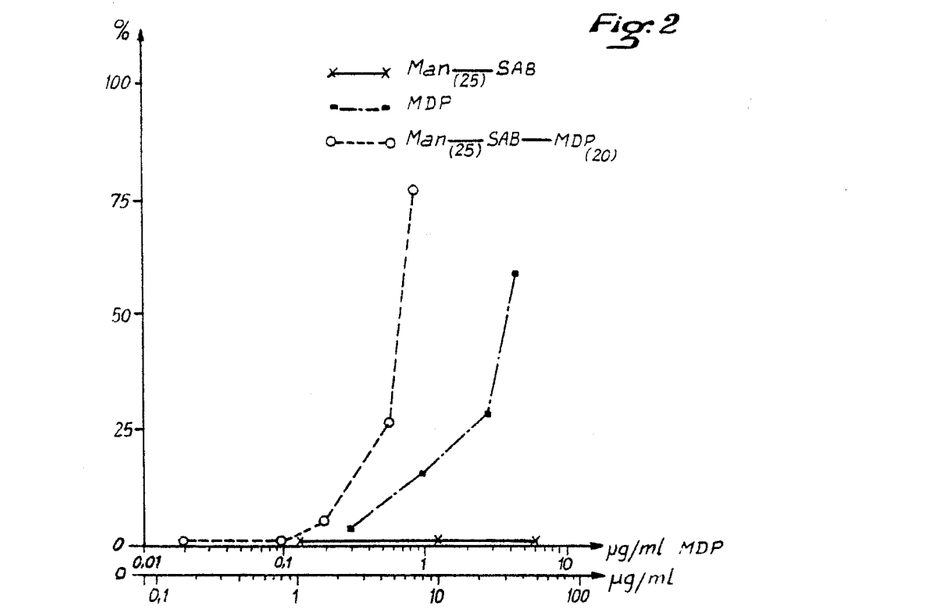
FIG. 2 represents the cytostatic effect of the peritoneal macrophages of mice treated with differing doses of free MDP or MDP conjugated to a neoglycoprotein (MAN-SAB) or LLC cells. Macrophage/LLC = 20.

The Man-SAB-MDP used contains 20 MDP residues per molecule of (Man)$_{25}$-SAB. Two types of target cells are used: L1210 leukemia cells (FIG. 1) and Lewis pulmonary carcinoma cells (LLC) (FIG. 2). The MDP, bonded to mannosyl-SAB makes the macrophages cytostatic vis-a-vis the two types of tumor cells employed. In addition, the bonded MDP is more active in vitro than free MDP, it acts in concentrations that are ten times weaker and very significantly increases the cytostatic effect of the macrophages.

TABLE 1

| Cytostatic Activity of Macrophages on L1210 and LLC Cells | | | |
|---|---|---|---|
| Processing of | Macrophage % cytostaticity | | |
| macrophages | Target Cells | L1210 | LLC |
| MDP | 20 | 10 | 15 |
|  | 40 | 12 | 20 |
| Man-SAB-MDP | 20 | 55 | 75 |
|  | 40 | 70 | 85 |

$4 \times 10^5$ macrophage are stimulated by 1 g/ml of free or bonded MDP.

After 24 hours, the target cells are are added in differing concentrations to obtain a macrophage/target cell ratio of 20 to 40 and are cocultivated for 24 hours. Four hours before the end of the culture period, 0.1Ci, 3.7 KBq of tritiated thymidine is added. The percentage of cytostaticity is calculated relative to the radioactivity incorporated by the activated target cells in the presence of untreated macrophages.

Macrophage/L1210 ratio = 20.

The percentage of cytostaticity is the average of the values of three independent cultures, plus 10%.

Figure 3:
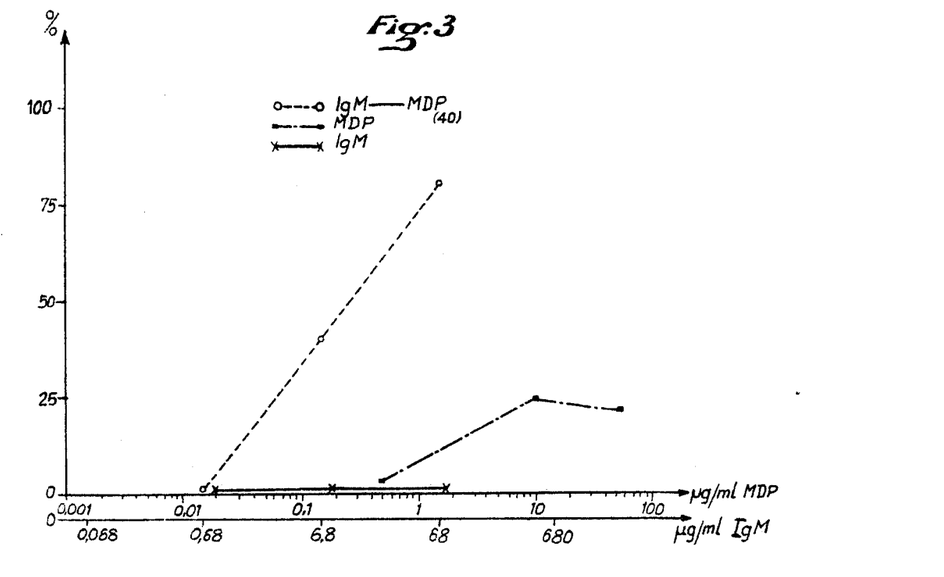
FIG. 3 represents the cytostatic effect of the peritoneal macrophages of mice treated with differing doses of free MDP or MDP conjugated to a monoclonal antibody (IgM) aimed at the L1210 target cell. Macrophage/L1210 ratio = 15.

The percentage of cytostaticity is the average of three cultures.

(5b) The conjugate of Example 15 [(6-P-α-Man)$_{20}$-SAB-(MDP)$_{15}$] was studied in a similar manner.

This compound has a marked affinity for the monocytes, which are strongly activated in this manner.

It should be noted that monocytes freshly prepared from circulating human blood do not possess a receiver for the mannose and are not activated by conjugates of the (α-Man)-SAB-(MDP) type.

Conversely, human monocytes recognize 6-phosphoryl mannose and, in the presence of a conjugate of the (6-P-α-Man)-SAB-(MDP) type, they become highly cytostatic and cytotoxic vis-a-vis the L1210 cells and the LLC cells.

(6) Application to the measurement of the cytostatic effect of macrophages stimulated by MDP conjugated to monoclonal antibodies (FIG. 3).

IgM anti L1210-MDP
IgM anti LLC-MDP

The cells are, respectively, L1210 leukemic cells and Lewis pulmonary carcinoma cells (LLC) which are combined with macrophages (macrophage/target cell ratio=15) and with monoclonal antibodies bonded to MDP. After 36 hours of incubation, $^3$H-tymidine is added to the culture. The cells are recovered and counted after 4 hours.

(7) Eradication of spontaneous metastases of Lewis's pulmonary carcinoma in C57 B16 mice after amputation of the limb containing a primary tumor.

The test principle is the folloiwng:

Injection of Lewis pulmonary carcinoma (LLC) tumor cells in the thigh of syngenic mice induce the formation of turmors. The growth of the metastases increases when the tumor is locally excised by surgery (Gorelik, E., et al., 21, 1980, 617–625); the volume of the metastases depends on the quantity of tumor cells injected and the date of amputation (Gorelik, E., et al., (1980), J.N.C.I. 65, 1257–1264).

$6 \times 10^6$ LLC cells prepared by treatement of a tumor with trypsine are injected into the thigh of a group of C57 B16 mice.

After nine days, the tumor (diameter: 1 cm) is removed by amputation of the limb at the thigh, after anasthesia. On the twelfth day, treatment is begun: Free or conjugated MDP (4 μg) is injected intravenously at three to four day intervals. At the end of the treatment, the development of the pulmonary metastases is measured by counting the incorporation of 5-iododeoxyuridine (or incorporated $^{125}$IUdR): Bonmassar, E., et al., 1975, Chemotherapy 21, 321–329).

There exists a relationship between incorporation of $^{125}$IUdR and the spread of the tumors. Fluorodeoxyuridine (25 μg/mouse) is injected interperitoneally into each animal, 30 minutes before injection of 1μCi (37 KBq) of $^{125}$IUdR in order to inhibit synthetasis thymidilate and in order for the cells to preferentially incorporate IUdR. After 24 hours, the mice are sacrificed, the lungs are weighed and their radioactivity is measured using a γ-scintigraph (LKB).

One group of seven mice is treated by injection of the (Man)$_{25}$-SAB-(MDP)$_{18}$ conjugate: Group A.

One group of seven mice, used as a control group, is treated by injection of an equivalent quantity of MDP and Man-SAB, in a mixture: Group B.

one group of seven healthy mice receive no treatment: Group C.

All of the mice in Group B, the control group, have an abundance of pulmonary metastases, measuring 2 to 3 mm in diameter, with the beginning of necrosis. Among the mice treated with the Man-SAB-MDP type conjugate, one displays metastases comparable to those of the control group, another displays several small pulmonary metastases (<1 mm in diameter), the lungs of the five remaining mice appear healthy.

The morphological observation is confirmed by measurement of the incorporation of $^{125}$I IUdR (Table 2). The average is:

625 cpm/100 mg of lung, Group A, for the five mice with lungs displaying a healthy appearance;

3,100 cpm/100 mg of lung, Group B (control). Lungs covered with metastases. Under these same conditions, the healthy mice, Group C, incorporate 800 cpm/100 mg of lung on average.

In conclusion, five mice out of seven were healed by injection of the Man-BSA-MDP compound, while seven mice out of the seven in the control group experienced abundant growth of metastases, as if no treatment were administered.

The tumor (10 mm in diameter) is removed on the twelfth day. Treatment consists of three intravenous injections of 4 μg of free or conjugated MDP three days after amputation. The pulmonary metastases are observed after the animal is sacrificed, or evaluated by incorporation of $^{125}$IUdR.

(a) cpm: mouse having a healthy appearance (5/7)
(b) cpm: mouse with metastases (2/7)

Another similar experiment has produced the following results, which are summarized in Table 2.

TABLE 2

Measurement of the incorporation of $^{125}$I in metastases in strokes per minute (Cpm)

| Treatment | Number of mice having: | | | | | |
|---|---|---|---|---|---|---|
| | Over 20 metastases | | 1 to 3 metastases | | 0 metastases | |
| | No. of mice | Cpm | No. of mice | Cpm | No. of mice | Cpm. |
| Controls | 7/7 | 4,000 | 0/7 | — | 0/7 | — |
| MDP + (Man) SAB Mixture | 7/7 | 3,700 | 0/7 | — | 0/7 | — |
| (Man)-SAB-(MDP) conjugate | 1/7 | 8,000 | 3/7 | 400 | 3/7 | 0 |

We claim:
1. A derivative of the formula

(R—X)$_m$—(LAM)

wherein
R is an N-acetylmuramylpeptidyl group or a derivative thereof;
(LAM is a neoglycoprotein having affinity for macrophages or monocytes, consisting of a protein covalenty substituted by more than 5 glycidic chains, each having at least 5 osidic units selected from α-D-glucose, α-D-mannose, α-L-fucose, N-acetylglucosamine, α-L-glucose, β-L-galactose, β-D-galactose, α-D-galactosamine, β-D-galactosamine, β-L-rhamose or 6-phosphorylα-D-mannose,
X is a covalent bond between a functional group of the peptidic part of R and a functional group of (LAM) or X is the residue of a conventional bifunctional coupling agent capable of bonding to R and (LAM) by formation of covalent bonds; and
m is a number greater than or equal to 1.
2. The derivative of claim 1 wherein one of said functional groups is an amine and the other is a carboxylic group, whereby X is an amide bond.
3. The derivative of claim 1 wherein said neoglycoprotein the said glycidic chains are bonded to said protein through a phenylthiocarbamyl bond, an azo group, an amide bond or an osidic bond.
4. The derivative of claim 3 wherein said glycidic chain is selected from the group consisting of: thiocarbamylphenyl-α-D-glucopyranoside, thiocarbamylphenyl-β-D-galactopyranoside,
thiocarbamylphenyl-α-D-mannopyranoside,
thiocarbamylphenyl-2-acetamido-2-deoxy-β-D-glucopyranoside,
thiocarbamylphenyl-α-L-fucopyranoside,
thiocarbamylphenyl-α-D-galactopyranoside,
thiocarbamylphenyl-α-L-rhamnopyranoside,
thiocarbamylphenyl-6-phosphoryl-α-D-mannopyranoside,
thiocarbamylphenyl-2-acetamido-2-deoxy-α-D-glucopyranoside,
thiocarbamylphenyl-2-acetamido-2-deoxy-α-D-glactopyranoside,
thiocarbamylphenyl-2-acetamido-2-deoxy-β-D-galactopyranoside,
thiocarbamylphenyl-β-D-glacto-pyranosyl-4-β-D-glucopyranoside,
azophenyl-β-D-galactopyranosyl-4-β-D-glucopyranoside,
azophenyl-α-D-glucopyranoside,
azophenyl-α-D-mannopyranoside,
azophenyl-α-L-fucopyranoside,
azophenyl-β-D-galactopyranoside and
azophenyl-2-acetamido-2-deoxy-β-D-glycopyranoside.

5. The derivative of claim 1 wherein said N-acetylmuramylpeptidyl group is selected from the group consisting of
N-acetylmuramyl-L-alanyl-D-isoglutaminyl,
N-acetylmuramyl-L-alanyl-D-isoglutaminyl-mesodiaminopimelyl,
N-acetylmuramyl-L-alanyl-D-isoglutaminyl-mesodiaminopimelyl-D-alanyl and
N-acetylmuramyl-L-alanyl-D-isoglutaminly-mesodiaminopimelyl-D-alanyl-D-alanyl.

6. A pharmaceutical composition comprising at least one derivative of claim 1.

7. A medication which is a stimulant of the cellular immune system comprising the derivative of claim 1.

8. A process for stimulating the activity of macrophages comprising administering to a host an effective amount of a derivative of the formula $$(R-X)_m-(LAM)$$

wherein
R is an N-acetyl muramyl peptidyl group or a derivative thereof,
(LAM) is a glycoconjugate selected from the group consisting of
(a) a neoglycoprotein having affinity for macrophages or monocytes, consisting of a protein covalently substituted by more than 5 glycidic chains, each having at least 5 osidic units selected from α-D-glucose, α-D-mannose, α-L-fucose, N-acetylglucosamine, α-L-glucose, β-L-galactose, β-D-galactose, α-D-galactosamine, β-D-galactosamine, β-L-rhamose or 6-phosphoryl-α-D-mannose, and
(b) natural or modified syngenic glycoproteins having affinity for macrophages or monocytes, containing residues selected from the group consisting of α-D-mannose, 6-phosphoryl-α-D-mannose and β-N-acetyl glucosamine.
X is a covalent bond between a functional group of the peptidic part of R and a functional group of (LAM) or X is the residue of a conventional bifunctional coupling agent capable of bonding to R and (LAM) by formation of covalent bonds; and
m is a number greater than or equal to 1.

9. The process of claim 1 wherein (LAM) is said neoglycoprotein.

* * * * *